United States Patent [19]

Smith et al.

[11] 4,104,302

[45] Aug. 1, 1978

[54] VINYLSULPHONE HARDENERS

[75] Inventors: Norman Alfred Smith, Hornchurch; Rainer Kitzing, Ingatestone, both of England

[73] Assignee: Ciba-Geigy AG, Basel, Switzerland

[21] Appl. No.: 734,781

[22] Filed: Oct. 22, 1976

[30] Foreign Application Priority Data

Oct. 31, 1975 [GB] United Kingdom ............... 45280/75

[51] Int. Cl.² .................. C07C 103/60; G03C 1/30
[52] U.S. Cl. .................. 260/561 S; 96/111; 96/112; 96/117; 260/553 E; 260/561 A
[58] Field of Search ........... 260/561 S, 561 A, 553 E; 96/111

[56] References Cited

U.S. PATENT DOCUMENTS

| | | | |
|---|---|---|---|
| 3,455,893 | 7/1969 | Froehlich | 96/111 |
| 3,642,486 | 2/1972 | Burness et al. | 96/111 |
| 3,868,257 | 2/1975 | Horii et al. | 96/111 |
| 3,978,122 | 8/1976 | Stauner et al. | 260/553 E |

OTHER PUBLICATIONS

Wagner et al., Synthetic Organic Chem., John W. Ley & Son, N.Y., N.Y., 1955, p. 566.

*Primary Examiner*—Arthur P. Demers
*Attorney, Agent, or Firm*—Burgess, Dinklage & Sprung

[57] ABSTRACT

Vinylsulphone compounds of the general formula

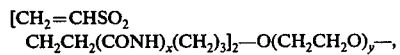

wherein $x$ is 1 or 2 and $y$ is 0 or an integer of 1 to 100 are provided. These compounds are useful as cross-linking agents for hydrophilic colloids, especially for gelatin which is in the form of layers of photographic materials.

4 Claims, No Drawings

VINYLSULPHONE HARDENERS

This invention relates to novel vinylsulphone compounds and to their production and use as cross-linking agents for hydrophilic colloids.

According to the present invention there are provided vinylsulphone compounds of the general formula $$[CH_2=CHSO_2CH_2CH_2(CONH)_x(CH_2)_3]_2-O(CH_2CH_2O)_y- \quad (1)$$

wherein $x$ is 1 or 2, and $y$ is 0 or an integer of 1 to 100.

Particularly useful compounds of formula (1) are those wherein $y$ is 0 or is an integer of 1 to 40. Most particularly useful compounds are those wherein $y$ is 0 or is an integer of 1 to 10 preferably of 1 to 4.

Thus the compounds of the present invention comprise two reactive end groups each containing a vinylsulphone group, these end groups being linked by a polyethylene oxide group or chain except for the simplest member of the class ($y = 0$) in which the end groups are linked by a simple oxygen atom.

Compounds of formula (1) wherein x is 1 may be prepared by reacting 2 molar proportions of 3-(2-chloroethylsulphonyl)-propionyl chloride with a molar proportion of a diamine of the general formula $$NH_2-(CH_2)_3-O(CH_2CH_2O)_y-(CH_2)_3NH_2 \quad (2)$$

wherein $y$ has the meaning assigned to it above, in a basic organic medium to produce a chloroethylsulphonyl compound of the general formula $$[ClCH_2-CH_2SO_2-CH_2-CH_2-CONH-(CH_2)_3]_2-O(CH_2CH_2O)_y- \quad (3)$$

wherein $y$ has the meaning assigned to it above and then converting (dehydrohalogenating) the chloroethylsulphonyl compound of formula (3) to the corresponding vinylsulphonyl compound to produce a compound of formula (1) wherein $x$ is 1.

Chloroethylsulphonyl compounds may be dehydrochlorinated to the corresponding vinylsulphonyl compounds in a number of different ways which are well known. Such conversions are described for example in U.S. Pat. No. 3,868,257 wherein triethylamine is used.

Diamines of formula (2) may be prepared by the cyanoethylation of the appropriate glycol and then by catalytic reduction as described by I. Nazarov et al. J. Gen. Chem. USSR. 24, 337 – 344 (1954) or by the method described in German Offenlegungsschrift No. 2,454,141. 3-(2-Chloroethylsulphonyl)-propionic acid may be prepared by the method described in French Pat. No. 1,363,046, wherein 2-chloroethyl sulphinic acid is reacted with acrylic acid and 3-(2-chloroethylsulphonyl)-propionyl chloride may be prepared therefrom by reaction with thionyl chloride.

Compounds of formula (1) wherein $x$ is 2 may be prepared by reacting a compound of the formula $$CH_2=CH(CONH_2(CH_2)_3-O-(CH_2CH_2O)_y-(CH_2)_3(NHCO)_2CH=CH_2 \quad (4)$$

wherein $y$ has the meaning assigned to it above with 2-chloroethyl sulphinic acid (prepared by reduction of β chloroethylsulphonyl chloride with alkali metabisulphite) to produce a chloroethylsulphonyl compound of formula $$[ClCH_2CH_2SO_2CH_2CH_2(CONH)_2(CH_2)_3]_2-O-(CH_2CH_2O)_y- \quad (5)$$

wherein $y$ has the meaning assigned to it above and then converting (dehydrohalogenating) chloroethylsulphonyl compound to the corresponding vinylsulphonyl compound to produce a compound of formula (1) wherein $x$ is 2.

The chloroethylsulphonyl compound may be dehydrochlorinated to the corresponding vinylsulphonyl compound as hereinbefore mentioned.

Compounds of formula (4) may be prepared by the method set forth British Patent Specification No. 1,419,213.

The compounds of formula (1) are of particular use in crosslinking hydrophilic colloids.

Therefore according to another aspect of the present invention there is provided a process for cross-linking hydrophilic colloids which contain amino, imino and/or hydroxyl groups characterised in that at least one compound of the above formula (1) is incorporated into the colloid to effect cross-linking thereof.

The crosslinking process of the present invention can be used in the textile and leather industry, the manufacture of paper and the plastics, glue and gelatin industry. Above all, it can be used as a process for hardening water-soluble colloids for example polyvinyl alcohol, gelatin or gelatin derivatives, especially when these colloids are in the form of layers of photographic material. The reaction of these colloids with the vinylsulphone compounds of the present invention takes place easily, and in the usual manner. The vinylsulphone compounds are very water-soluble and thus can be used as aqueous solutions.

In most cases in order to carry out the cross-linking process of the present invention it suffices to add the vinylsulphone compounds of the present invention as an aqueous solution or in a solid form which is as finely divided as possible, to an aqueous solution of the hydrophilic colloid, with good stirring.

Thus, a solution of the vinylsulphone crosslinking agent in water, or mixed with, for example, ethanol, methanol or acetone, can be brought together with the colloids at normal or slightly raised temperature. Gelatin, which optionally may contain silver halide and/or other components required to produce photographic images, has proved particularly suitable for cros,-linking by the process of the present invention.

The coating solution which is an aqueous solution containing both gelatin and the vinylsulphone cross-linking agent can, in the usual way, be coated on a substrate to form a layer, and be dried. The layer can then be left at elevated temperature or at room temperature for a certain time, for example up to 24 hours. Thereupon cross-linking, which is evidenced by hardening of the layer, takes place rapidly and progressively; thus shown by the melting point of the gelatin being raised substantially, for example from 25° to 60° C, and by the reciprocal swelling factor increasing.

The amount of the vinylsulphone cross-linking agent used depends on the desired degree of hardening of the gelatin layer required but is suitably from 0.1 to 10 percent by weight based on the weight of the dry gelatin.

A particular advantage of the process of the present invention is that when the vinylsulphone cross-linking agents are used at a low concentration they impart a sufficient degree of hardness to the gelatin layers in 18 to 24 hours, so that the coated material can be tested by processing a sample immediately following its manufacture, even if the test be carried out at a raised temperature or in strong processing baths.

It is a further advantage that during the process of the present invention, no significant change in the pH value of the gelatin layer occurs.

The cross-linking or hardening effect itself is very stable; even after prolonged storage at temperatures around 40° C and at a relative atmospheric humidity of about 70%, the reciprocal swelling factor remains above 0.2 (compare Table 1).

Further the degree of hardening is also not changed significantly by acids or bases even on prolonged action, which indicates that the hardener-gelatin bond created has great resistance to hydrolysis.

The vinylsulphone compounds of the present invention are furthermore generally sufficiently soluble in water and sufficiently stable in aqueous solutions to enable the process of the present invention to be used in the preparation of photographic material. Thus, for example, it is particularly desirable — for the continuous manufacture of photographic materials — that batches of solutions of cross-linking agents should remain stable at room temperature for several hours or days and that their concentration should not decrease or should only do so insignificantly. Also it is important that in the coating solution, at about 40° C, the hardener should undergo very little or no decomposition and very little or no reaction with water during the requisite standing time and dwell time, so as to maintain its full cross-linking action over the course of several hours, during coating, drying and storage of the photographic material.

Furthermore, the viscosity of the coating solution should not significantly increase during the standing time as a result of the addition of the hardener. It is also particularly important that even on prolonged treatment of the coated layer at raised temperature and atmospheric humidity conditions the hardener should not cause any yellowing, fogging of photographic material or effect on the graduation of the material on development.

The vinylsulphone compounds of the present invention fulfil the above desiderata very well. In particular they hydrolyse very little when present in an aqueous solution. They do not discolour gelatin. When these compounds are added to a gelatin solution they cause only a small increase in the viscosity of the solution and thus such solutions can be coated without difficulty. The compounds have a good hardening effect over a wide pH range and thus can be used in the preparation of a wide range of photographic materials.

Thus the process of the present invention is suitable for hardening (cross-linking) all the layers in photographic material containing gelatin for example, intermediate layers, emulsion layers, base layers, top layers, backing layers and anti-halation layers. The layers can contain not only the cross-linking agents but also the additives of the most diverse kind for example, silver halide, pigments, such as barium sulphate, titanium dioxide or silicon dioxide or those of organic nature, such as coloured pigments, and also image dyestuffs, colour coupling agents, latices, sensitisers, filter dyestuffs, antihalation dyestuffs and light screening dyestuffs, emulsion stabilisers, UV absorbers, optical brighteners and even other cross-linking agents.

The present invention not only includes the novel vinylsulphones of formula (1), the processes for preparing these compounds, the process for cross-linking hydrophilic colloids using the vinylsulphones of formula (1) but also includes hydrophilic colloids cross-linked by the above cross-linking process and in particular includes layers containing gelatin so cross-linked especially gelatino silver halide emulsion layers and other layers in photographic material as well as the photographic material containing such layers.

The following Example I shows the preparation of a vinylsulphone of formula (1) wherein $x$ is 1, Example II shows the preparation of a vinylsulphone of formula (1) wherein $x$ is 2 and Example III shows the use of the compounds of formula (1) to cross-link a hydrophilic colloid (gelatin).

EXAMPLE I

Preparation of
Oxybis-[N-propyl-3-vinylsulphonylpropionamide]
(Hardener 1.)

3-(2-chloroethylsulphonyl)-propionyl chloride (Stage 1.)

20 g of 3-(2-chloroethylsulphonyl)-propionic acid was mixed with 70 ml thionyl chloride and the mixture refluxed for 2 hours. Excess thionyl chloride was distilled off under reduced pressure and the product recrystallised from benzene/petrol.

Yield 18.5 g Mp. 71° – 72° C.

Oxybis-[N-propyl-3-(2-chloroethylsulphonyl)propionamide] (Stage 2)

4.38 g 3-(2-chloroethylsulphonyl)-propionyl chloride was dissolved in 60 ml dry dichloroethane and treated with a solution of 1.32 g bis-(3-aminopropyl)-ether and 2.02 g triethylamine in 40 ml dry dichloroethane at 5° – 10° C. The mixture was stirred for a further 2 hours then the solid was filtered, washed with dichloroethane and dried. The product was recrystallised from ethanol.

Yield 2.8 g Mp. 156° – 157° C.

Oxybis-[N-propyl-3-vinylsulphonyl-propionamide] (Stage 3)

2.0 g of the preparation of stage 2 was suspended in 30 ml ethanol, 0.87 g of triethylamine added and warmed to 50° C. The mixture was stirred for 20 minutes, the solution filtered and the filtrate evaporated under reduced pressure. The product was recrystallised from methanol.

Yield 1.3 g Mp. 110° – 112° C.

Other vinylsulphones of formula (1) wherein $x$ is 1 were prepared analogously. To make the compound of formula (1) wherein $x$ is 1 and $y$ is 1 the amine used in stage 2 of the above preparation was 3,3'-(ethylenedioxy)-dipropylamine (hardener 2). To make the compound of formula (1) wherein $x$ is 1 and $y$ is 2 the amine used in stage 2 of the above preparation was oxybis-(ethyleneoxypropylamine) (hardener 3). To make the compound of formula (1) wherein $x$ is 1 and $y$ is 4 the amine used in stage 2 of the above preparation was oxybis-(ethyleneoxyethyleneoxypropylamine) (hardener 4).

EXAMPLE II

Preparation of the compound of the formula

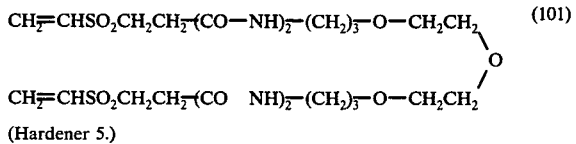

(Hardener 5.)

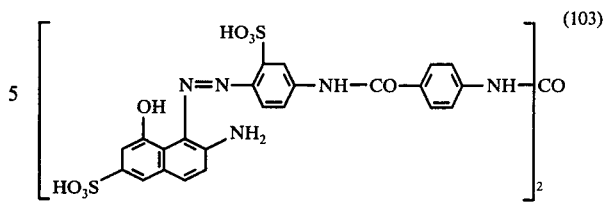

A solution of 8.3 g sodium metabisulphite in 40 ml H$_2$O was cooled to 5° to 10° C, and 12.2 g β-chloroethylsulphonyl chloride added dropwise maintaining pH≃5 by addition of 25% aqueous sodium hydroxyde solution. The mixture was stirred a further ½ hour at 5° to 10° C then 7.5 g of 49% H$_2$SO$_4$ added slowly and cooled to 0° to 5° C. After ½ hour stirring the precipitated sodium sulphate was filtered off and washed through with a little cold water. To the filtrate was added a solution of the compound of the formula

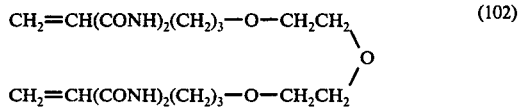

(as prepared in British Patent Specification No. 1,419,213) 10.3 g in 50% aqueous ethanol, stirred 3 hours at 5° to 10° C then left for 48 hours at 0° C. The product was filtered, washed with water, ethanol and air dried.

Yield 6 g. Mp. 110° to 115° C.

5.36 g of the above compound was suspended in 80 ml butan-2-one at 30° to 35° C. 2.0 g triethylamine was added and the mixture stirred for 1 hour at 30° C, then cooled in ice. The solution was filtered and the filtrate evaporated under reduced pressure to give non-crystallisable viscous oil.

Yield 4.0 g.

EXAMPLE III

In the Example which follows, the reciprocal swelling factor is used as a measure of the hardening. The samples were prepared as follows:

6 ml of a 3% strength gelatine solution, 1 ml of a 1% strength dyestuff solution of the formula 1 ml of a 25.10$^{-3}$ molar solution of hardener 1 and 5 ml of deionised water are mixed and the pH adjusted to 6.5. The solution is coated on a 13 × 18 cm triacetate film. After solidification at 10° C, the layer is dried over the course of 2 hours at approx. 20° C. (The dyestuff merely serves to make the samples more readily visible during the swelling measurements.) Some samples of the coated film were stored under room conditions (NK, approx. 20° C, 50% relative atmospheric humidity) and other samples were incubated (CL, 43° C, 69% relative atmospheric humidity). Similar solutions of hardeners 2 to 5 were also prepared and tested.

To determine the reciprocal swelling factor, a thin section of approx. 20 μ is prepared from each of the samples and measured under a microscope. The thickness of the dry gelatin layer is then determined, deionised water is then added and after 4 minutes the thickness of the swollen gelatin layer is measured. The reciprocal swelling factor 1/SF corresponds to the following ratio:

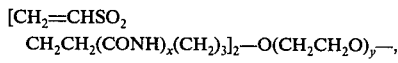

Table 1

| Hardener | Storage | 1/SF 3 hrs. | 2 days | 7 days | 14 days |
|---|---|---|---|---|---|
| 1 | NK | 0.172 | 0.238 | 0.328 | 0.307 |
|   | CL |       | 0.275 | 0.300 | 0.293 |
| 2 | NK | 0.147 | 0.262 | 0.331 | 0.313 |
|   | CL |       | 0.287 | 0.367 | 0.357 |
| 3 | NK | 0.096 | 0.177 | 0.236 | 0.284 |
|   | CL |       | 0.222 | 0.234 | 0.296 |
| 4 | NK | 0.110 | 0.209 | 0.258 | 0.283 |
|   | CL |       | 0.255 | 0.263 | 0.320 |
| 5 | NK | 0.187 | 0.218 | 0.198 | 0.234 |
|   | CL |       | 0.219 | 0.235 | 0.255 |

What we claim is:

1. A vinylsulphone compound of the general formula

[CH$_2$=CHSO$_2$CH$_2$CH$_2$(CONH)$_x$(CH$_2$)$_3$]$_2$—O(CH$_2$CH$_2$O)$_y$—, wherein x is 1 or 2, and y is 0 or an integer of 1 to 100.

2. A vinylsulphone compound according to claim 1, wherein y is 0 or is an integer of 1 to 40.

3. A vinylsulphone compound according to claim 2, wherein y is 0 or is an integer of 1 to 10.

4. A vinylsulphone compound according to claim 3, wherein y is 0 or an integer of 1 to 4.

* * * * *